United States Patent [19]

Bärwald et al.

[11] Patent Number: 4,758,515

[45] Date of Patent: Jul. 19, 1988

[54] PROCESS FOR THE PREPARATION OF A LOW-GLUCOSE DIGESTION PRODUCT FROM INULIN-CONTAINING PARTS OF PLANTS

[75] Inventors: Günter Bärwald, Berlin; Erhard F. Flöther, Kassel, both of Fed. Rep. of Germany

[73] Assignee: Gunter Barwald, Berlin, Fed. Rep. of Germany

[21] Appl. No.: 837,306

[22] Filed: Mar. 7, 1986

[30] Foreign Application Priority Data

Mar. 8, 1985 [DE] Fed. Rep. of Germany ....... 3508387

[51] Int. Cl.$^4$ .................. C12P 19/14; C12P 19/04; C12P 19/02; A23G 3/00
[52] U.S. Cl. ............................ 435/99; 435/101; 435/105; 426/51; 426/658
[58] Field of Search ............... 435/99, 101, 105, 800, 435/276, 137

[56] References Cited

U.S. PATENT DOCUMENTS

| | | | |
|---|---|---|---|
| 3,935,071 | 1/1976 | Bergmeyer et al. | 435/137 |
| 4,277,563 | 7/1981 | Kerkhoffs | 435/99 |
| 4,345,031 | 8/1982 | Coppens | 435/137 |
| 4,397,949 | 8/1983 | Peters et al. | 435/99 |
| 4,421,852 | 12/1983 | Hoehn et al. | 435/99 |
| 4,460,686 | 7/1984 | Hartmeier | 435/137 |
| 4,478,854 | 10/1984 | Adler-Nissen et al. | 435/99 X |

*Primary Examiner*—Lionel M. Shapiro
*Attorney, Agent, or Firm*—Dressler, Goldsmith, Shore, Sutker & Milnamow, Ltd.

[57] ABSTRACT

Process for the preparation of a low-glucose digestion product from inulin-containing parts of plants, the parts of plants being comminuted, and the inulin being degraded to fructose or fructose oligomers. The process comprises a suspension of the comminuted parts of plants in an aqueous medium, or a pressed juice or extract obtained therefrom, being heated, without removal of the inulin, at temperatures up to 100° C., until the enzymes intrinsic to the plant have substantially been inactivated, whereupon, after cooling, inulinase is added to the suspension or the pressed juice or the extract.

14 Claims, No Drawings

PROCESS FOR THE PREPARATION OF A LOW-GLUCOSE DIGESTION PRODUCT FROM INULIN-CONTAINING PARTS OF PLANTS

DESCRIPTION

The invention relates to a process for the preparation of a low-glucose digestion product from inulin-containing parts of plants.

It is known that the carbohydrate inulin which is stored in various energy-providing, inulin-containing parts of plants, for example in Jerusalem artichoke tubers, dahlia tubers or chicory roots, can be digested by steam processes, acid treatment at the boiling point, or by comminution and extraction, and can be degraded as far as the monosaccharides fructose and glucose. The inulin-containing parts of plants contain enzymes which are intrinsic to the plant, which are not specifically described in detail and which can hydrolyze inulin as far as fructose and glucose. Pure inulin contains about 3% glucose and about 97% fructose, the glucose residue being located in the terminal position to the polymeric fructose which is bonded $\beta$-1,2 to form chains. The proportion of glucose in the tuber and root material from the said plants is higher, namely between 5 and 15%, because the polymeric fructose may have shorter chains depending on the time of harvesting of the tubers.

Considerable losses of sugar from inulin stored in tubers or roots occur in the acid digestion and steam processes, namely and especially owing to caramelization and browning products, and owing to the formation of difructose dianhydride.

Furthermore, it is known to degrade inulin to fructose by the action of the enzymes which are intrinsic to the plant and are contained in the inulin-containing parts of plants; however, the yield of fructose is low, and the hydrolysis time extends over several days. Furthermore, it has been found, surprisingly, that the proportion of glucose in the hydrolysate is higher than in the starting material. This probably derives from the fact that the fructose is isomerized to glucose by the catalytic action of the enzymes intrinsic to the plant. The advantage which is achieved by the enzymatic degradation by the enzymes intrinsic to the plant over the acid digestion and steam processes with regard to a high fructose content and low glucose content is thus partly abolished again owing to a certain proportion of the free fructose being converted into free glucose by isomerization.

A relatively high glucose content interferes especially when the digestion product is to be used as a dietetic product or as food for diabetics or as intermediate for the preparation of pure fructose or fructose oligomers.

The invention thus has the object of making available a process for the preparation of a low-glucose digestion product from comminuted, inulin-containing parts of plants, in which the inulin is degraded in high yield to give fructose, and a high proportion of fructose oligomers is degraded without free glucose being formed in a side reaction or secondary reaction.

This object is achieved by the process according to the invention in that a suspension of the comminuted parts of plants in aqueous medium, or a pressed juice or extract obtained therefrom, is heated at temperatures up to 100° C. until the enzymes intrinsic to the plant have substantially been inactivated, whereupon, after cooling, inulinase is added to the suspension or the pressed juice or the extract.

Although the process according to the invention can be applied to all inulin-containing parts of plants, the inulin-containing parts of plants which are preferably used are Jerusalem artichoke tubers, dahlia tubers or chicory roots, which are available in relatively large quantities as commercial products.

The inulinases used according to the invention are known per se (compare, for example, "Starch", 1981, pages 373-377; J. Chem. Tech. Biotechnol, 1984, 34B, 45-51). Their application for the degradation of inulin from inulin-containing parts of plants to give fructose has also been disclosed. However, their application for the preparation of low-glucose digestion products and fructose oligomers has not been disclosed.

The fructose oligomers are soluble bulk materials which, like inulin, display a very low insulinogenic action. In contrast to pure fructose, a mixture of fructose and fructose oligomers results in a lower triglyceride level in the blood. Thus, for dietetic applications of the digestion product according to the invention, it is advantageous to set the ratio by weight of fructose to fructose oligomers to inulin at 1.5–3:1:0–1.5. The term fructose oligomers is to be understood in this context to mean those having 2 to 10 fructose units.

The inulinases which are preferably used according to the invention are those obtained from molds of the genera Aspergillus, Penicillium and Fusarium and/or from certain yeasts of the genera Kluyveromyces, Saccharomyces and Candida but the choice is not restricted to these species.

The inulinases act in a wide pH and temperature range, the reaction rate being dependent on the substrate concentration, the enzyme quantity and the specific optimal pH and temperature for the particular inulinase. The optimal pH conditions for digestion of Jerusalem artichoke tubers are at about 5.1. It is furthermore known that the inulinases have exogenous and endogenous hydrolysis functions, the endogenous inulinases hydrolyzing the inulin molecules with longer chain length to subunits with shorter chain lengths, which are composed of fructose oligomers, whereas the exogenous inulinases eliminate first the terminal glucose units, and then the particular fructose units which are then terminal, from the inulin. The endogenous inulinases are preferred according to the invention.

In carrying out the process according to the invention, first the inulin-containing parts of plants are comminuted mechanically, some of the cells being destroyed, so that inulin is available as a substrate for the subsequent enzymatic digestion. The comminution of the parts of plants can be carried out with, for example, the use of screening or hammer mills or with the use of slicing machines, the comminution resulting in a particle size between 0.5 and 25 mm. For example, hammer mills with mesh sizes of 1.0 and 1.5 mm have been tried out, as have slicing machines for sugar beet with slice diameters of 25 mm. The comminuted parts of plants can now either be extracted or further comminuted to form a pulp which is, where appropriate, converted into a free-flowing suspension by addition of water. The proportion of water is normally 10 to 180%, preferably 20 to 50%, of the inulin-containing parts of plants.

To inactivate the enzymes intrinsic to the plant, the pH of the suspension or of the aqueous extract is generally adjusted to 3.0 to 7.0, preferably to 3.5 to 5.5, whereupon the suspension or the aqueous extract is generally heated at 70° to 100° C., preferably at 80° to 90° C. The heating time depends on the temperature used and is between about 10 minutes and 1 hour, preferably about 30 minutes. Heating at above 100° C. should be avoided because, as already said, at these high temperatures considerable losses of sugar owing to caramelization and browning reactions and owing to the formation of difructose dianhydride occur.

After the heating, the suspension or the pressed juice or the extract is cooled to temperatures of about 30° to 80° C., preferably to temperatures between 40° and 65° C., and is normally adjusted to a pH of about 3 to 6 using acids (using the approved edible acids for final foodstuff products). The inulinases are then added. The exposure time depends on the temperature, the inulinase used and the desired degree of digestion. If, for example, fructose oligomers are required, then endogenous inulinase is preferably used, or the exposure time is kept shorter than that for the production of monomeric fructose.

The pH and temperature conditions which are employed for the enzymatic digestion are preferably those lying in the range of optimal activity. For example, the pH values when inulinases from Candida or Kluyveromyces yeasts are used are between 3.5 and 5.5, and the temperatures are between 35° and 55° C.; when inulinases from molds are used, the pH values are between 3.5 and 7.0, and the temperatures are between 40° and 65° C.

The enzymatic digestion can be stopped by heating the suspension or the pressed juice or the extract, thus deactivating the inulinase. The heating can be combined with evaporation (for example at 80° C. in vacuo) if, for example, a concentrated digestion product is required.

In a preferred embodiment of the invention, the glucose content of the digestion product can be reduced by oxidation of the terminal glucose groups in the inulin to gluconic acid by passing oxygen, or a gas contain oxygen, through the suspension or the pressed juice or the extract, with the addition of glucose oxidase and catalase. An enzyme mixture of this type is disclosed in German Patent Specification No. 2,520,792. In that case it is used as an antioxidant to remove oxygen from fermented and unfermented beverages, to which glucose has been added where appropriate. In contrast, in the present case it is used for the catalytic oxidation of the glucose. The enzyme mixture can be adsorbed onto an inert adsorbent, such as silica gel, porous glass coated with silicon hydroxide, or aluminum oxide, silicates (in particular bentonite) or zeolites. The enzyme mixture comprising glucose oxidase and catalase, as well as the oxygen or the gas containing oxygen, can be added to the aqueous medium before, during or after the enzymatic digestion with inulinase. The concentration of the oxygen dissolved in the aqueous medium is preferably adjusted to between 0.1 and 1 mg $O_2$/liter. These oxygen concentrations are relatively low, so that damage due to oxidation of the other constituents (for example vitamins and flavorings) of the digestion product is avoided.

The invention also relates to the use of the digestion products, obtained by the process according to the invention, as dietitic products, as food for diabetics and/or as intermediates for obtaining fructose or fructose oligomers. The digestion products according to the invention are preferably used in the form of pressed juices or pressed juice concentrates.

The process according to the invention is so mild that sensitive substances contained in the inulin-containing parts of plants are not damaged. These include, for example, vitamins, proteins, unsaturated fats and flavorings.

The invention is illustrated by the examples which follow.

EXAMPLE 1

3.6 tons of Jerusalem artichoke tubers (previously thoroughly washed) were mechanically comminuted in a mill so that the particle size was preferably below 1.5 mm. 1,400 liters of water were added to the pulp so that it could be pumped and agitated. The suspension had an initial pH of 6.3; acidification was carried out throught the process, using solid citric acid (monohydrate), so that the pH was between 4.5 and 5. Immediately after the mechanical breaking down the suspension was heated, by tubular heat-exchangers, to 80° C., maintained at this temperature for 30 minutes, and cooled to 60° C. by the countercurrent principle. 3 units of inulinase per gram of inulin (the inulin content of the tubers had been determined beforehand) were added to the suspension for the hydrolysis. The quantities of the free monosaccharides fructose and glucose formed in the suspension were determined by chromatography (HPLC) and biochemically (enzymatic methods, Boehringer tests). In a second experiment, 1,250 kg of Jerusalem artichoke tubers were mechanically comminuted as before and suspended in 485 liters of water. This suspension was heated only to 60° C., adjusting the pH to 4.5 to 5. The same amount of enzyme was added as before. The formation of the monosaccharides fructose and glucose was determined quantitively as described before. The results of the experiments are shown in Table I.

TABLE I

| | Fructose g per g of tubers | Glucose g per g of tubers | Ratio fructose:glucose | Free monosaccharides as a percentage of the total sugars in the tubers (degree of saccharifacation) |
|---|---|---|---|---|
| A. After mechanical breaking down | 1.2 | 0.4 | 1:0.33 | 0.9 |
| After heating at 80° C. (inactivation of the enzymes intrinsic to the plant) 1 hour enzymatic hydrolysis | 34.2 | 7.2 | 1:0.21 | 23.7 |
| As before but after 2 hours enzymatic hydrolysis | 48.7 | 9.1 | 1:0.18 | 33.0 |
| B. Without heating (no | 31.5 | 8.2 | 1:0.26 | 22.7 |

TABLE I-continued

|  | Fructose g per g of tubers | Glucose g per g of tubers | Ratio fructose:glucose | Free monosaccharides as a percentage of the total sugars in the tubers (degree of saccharifacation) |
| --- | --- | --- | --- | --- |
| inactivation of the enzymes intrinsic to the plant) 1 hour enzymatic hydrolysis at 60° C. As before but after 2 hours enzymatic hydrolysis | 42.2 | 11.9 | 1:0.28 | 30.9 |

The results of the experiments show that the ratio of fructose to glucose is highest when the enzymes intrinsic to the plant are inactivated before the treatment with inulinase.

EXAMPLE 2

A pressed juice (specific gravity=1.070; pH=4.7) was prepared from a Jerusalem artichoke suspension treated as in Example 1 (Experiment A; 2 hour enzymatic hydrolysis). The pressed juice was concentrated in a falling film evaporator, at temperatures below 65° C. in vacuo, to the specific gravity of 1.070. 250 ml of the pressed juice, at 50° C., were mixed with commercially available glucose oxidase/catalase (GOD 155) which was suspended in the liquid. Using a sintered disk, air was continuously passed into the vessel from below, the stream of air being adjusted so that a maximum of 1 mg $O_2$/liter was dissolved (measured with an Oxi-oxygen measuring device and an oxygen electrode). The decrease in the glucose content is shown in Table II.

TABLE II

Start: 13 g glucose/liter Jerusalem artichoke pressed juice
after 1 hour=5 g glucose/liter Jerusalem artichoke pressed juice
after 2 hour=2.5 g glucose/liter Jerusalem artichoke pressed juice
after 3 hour=1 g glucose/liter Jerusalem artichoke pressed juice The resulting pressed juice is thus relatively low in glucose and can be used as a beverage for diabetics.

Comparison Example

Jerusalem artichoke tubers were passed through a screen with a slit width of 1.5 mm. Water was added to the tuber pulp to the extent of one half its weight. One portion of the pulp thus diluted was agitated at 18° C., and another portion was allowed to stand at 41° C., for hydrolysis. The amounts of fructose and glucose formed were determined and converted to dry mass of tuber material. The hydrolysis temperature of 41° C. corresponds to the temperature of optimal activity of the inulinase contained in the Jerusalem artichoke tubers. The results are shown in Table III.

TABLE III

| Exposure time |  | Initial sample | 2 days | 5 days | 9 days |
| --- | --- | --- | --- | --- | --- |
| Fructose content g per kg dry mass of tubers | 41° C. = | 1.7 | 145 | 246 | 366 |
|  | 18° C. = | 1.7 | 31 | 66 | not determined |
| Glucose | 41° C. = | 0.2 | 41 | 86 | 131 |

TABLE III-continued

| Exposure time | Initial sample | 2 days | 5 days | 9 days |
| --- | --- | --- | --- | --- |
| content g per kg dry mass of tubers | 18° C. = 0.2 | 9 | 23 | not determined |

The data related to the dry mass were made necessary by evaporation losses resulting because of the long standing time at the temperatures indicated.

It is seen that there is pronounced formation of glucose, which is probably caused by isomerization reactions taking place in the aqueous material composed of comminuted tubers and catalyzed by the enzymes intrinsic to the plant.

Analysis immediately after the mechanical breaking down of the Jerusalem artichoke tubers shows a ratio of 1.7 parts by mass of fructose to 0.2 parts by mass of glucose; this corresponds to a ratio of about 88.2% fructose to about 11.8% glucose, or a fructose/glucose ratio of 1:0.12. The proportion of free fructose increases during the hydrolysis. Because of the structure of inulin (terminal glucose groups), if only hydrolysis were to take place the ratio between the monosaccharides ought to change in favor of fructose. However, the opposite occurs, that is to say proportionately too much free glucose is formed. The fructose/glucose ratio after 2 days (at 41° C.) is 1:0.28, and it is as much as 1:0.35 after 5 days. This finding can only be explained by isomerization of the fructose to glucose by the action of the enzymes intrinsic to the plant.

What is claimed is:

1. Process for the preparation of a low-glucose digestion product from inulin-containing parts of plants, the parts of plants being comminuted, and the inulin being degraded to fructose and fructose oligomers, which comprises a suspension of the comminuted parts of plants in an aqueous medium, or a pressed juice obtained therefrom, being heated without removal of the inulin, at temperatures up to 100° C., until the enzymes intrinsic to the plant have substantially been inactivated, whereupon, after cooling, inulinase is added to the suspension or the pressed juice, the digestion being controlled so that a ratio by weight of fructose to fructose oligomer to inulin of 1.5–3:1:0–1.5 is reached.

2. A process as claimed in claim 1 wherein Jerusalem artichoke tubers, dahlia tubers or chicory roots are used as said inulin-containing parts of plants.

3. A process as claimed in claim 1 wherein inulinase obtained from molds of the genera Aspergillus, Penicillium and Fusarium and/or from yeasts of the genera Kluyveromyces, Saccharomyces and Candida is used.

4. A process as claimed in claim 2 wherein inulinase obtained from molds of the genera Aspergillus, Penicillium and Fusarium and/or from yeasts of the genera Kluyveromyces, Saccharomyces and Candida is used.

5. A process as claimed in claim 1 wherein the comminution of the parts of plants is carried out using screening or hammer mills or using slicing machines, down to a particle size between 0.5 and 25 mm.

6. A process as claimed in claim 1 wherein the pH of the suspension is adjusted to 3.0 to 7.0, and the suspension or the pressed juice is heated at 70° to 100° C.

7. A process as claimed in claim 4 wherein the pH of the suspension is adjusted to 3.5 to 5.5, and the suspension or the pressed juice is heated at 80° to 90° C.

8. A process as claimed in claim 1 wherein the inulinase is added at temperatures between 40° and 65° C.

9. A process as claimed in claim 4 wherein the inulinase is added at temperatures between 40° and 65° C.

10. A process as claimed in claim 7 wherein the inulinase is added at temperatures between 40° and 65° C.

11. A process as claimed in claim 1 wherein the glucose derived from the terminal glucose groups of the inulin is oxidized to gluconic acid by passing oxygen, or a gas containing oxygen, through the suspension or the pressed juice, with the addition of glucose oxidase and catalase.

12. A process as claimed in claim 4 wherein the glucose derived from the terminal glucose groups of the inulin are oxidized to gluconic acid by passing oxygen, or a gas containing oxygen, through the suspension or the pressed juice, with the addition of glucose oxidase and catalase.

13. A process as claimed in claim 7 wherein the glucose derived from the terminal glucose groups of the inulin are oxidized to gluconic acid by passing oxygen, or a gas containing oxygen, through the suspension or the pressed juice, with the addition of glucose oxidase and catalase.

14. A process as claimed in claim 12 wherein the concentration of the oxygen dissolved in the aqueous medium is adjusted to between 0.1 and 1 mg $O_2$/liter.

* * * * *